(12) United States Patent
Teichtmann

(10) Patent No.: US 9,138,128 B2
(45) Date of Patent: Sep. 22, 2015

(54) MEDICAL INSTRUMENT

(75) Inventor: Elmar Teichtmann, Heilbronn (DE)

(73) Assignee: Richard Wolf GmbH, Knittlingen (DE)

( * ) Notice: Subject to any disclaimer, the term of this patent is extended or adjusted under 35 U.S.C. 154(b) by 206 days.

(21) Appl. No.: 13/423,394

(22) Filed: Mar. 19, 2012

(65) Prior Publication Data

US 2012/0238808 A1    Sep. 20, 2012

(30) Foreign Application Priority Data

Mar. 19, 2011   (DE) .......................... 10 2011 014 543

(51) Int. Cl.
| | |
|---|---|
| *A61B 1/00* | (2006.01) |
| *A61B 1/06* | (2006.01) |
| *G01B 7/30* | (2006.01) |
| *H01F 7/00* | (2006.01) |
| *A61B 1/045* | (2006.01) |
| *H03K 17/97* | (2006.01) |
| *A61B 17/00* | (2006.01) |

(52) U.S. Cl.
CPC ......... *A61B 1/00025* (2013.01); *A61B 1/00066* (2013.01); *A61B 1/045* (2013.01); *H03K 17/97* (2013.01); *A61B 2017/0042* (2013.01); *A61B 2017/00367* (2013.01); *H03K 2217/94068* (2013.01)

(58) Field of Classification Search
USPC ............... 600/101, 109, 130, 131, 160–181; 606/169, 171, 180; 173/213–218; 324/207.25; 335/219
See application file for complete search history.

(56) References Cited

U.S. PATENT DOCUMENTS

| | | | |
|---|---|---|---|
| 4,036,311 | A | 7/1977 | Goof |
| 6,945,981 | B2 | 9/2005 | Donofrio et al. |
| 7,619,499 | B2 * | 11/2009 | Wieler et al. .................. 335/285 |
| 2002/0022763 | A1 | 2/2002 | Sano et al. |
| 2008/0272869 | A1 * | 11/2008 | Takayama et al. ............ 335/219 |
| 2009/0160587 | A1 | 6/2009 | Gailledrat |
| 2010/0125166 | A1 | 5/2010 | Henzler |
| 2011/0073342 | A1 | 3/2011 | Gilsdorf et al. |

FOREIGN PATENT DOCUMENTS

| | | | |
|---|---|---|---|
| DE | 2509201 | A1 | 9/1975 |
| DE | 29823773 | U1 | 12/1999 |
| DE | 60126243 | T2 | 11/2007 |
| DE | 102007038358 | A1 | 2/2009 |
| DE | 102008057734 | A1 | 5/2010 |
| GB | 1101367 | A | 1/1968 |
| JP | 09-019404 | A | 1/1997 |
| WO | 9714350 | A1 | 4/1997 |
| WO | WO 2009021718 | A2 * | 2/2009 ................ H01F 1/00 |

OTHER PUBLICATIONS

Pre-Search Report issued Nov. 16, 2012 in AT Application No. 50081/2012.
Search Report issued Jun. 13, 2012 in GB Application No. GB1204571.2.
Office Action issued Jan. 4, 2012 in DE Application No. 10 2011 014 543.5.

\* cited by examiner

*Primary Examiner* — Ryan Henderson
(74) *Attorney, Agent, or Firm* — Panitch Schwarze Belisario & Nadel LLP

(57) ABSTRACT

A medical instrument includes a handle, on which at least one electric switch is arranged. The switch has an annular mechanical actuation unit whose outer side forms a grip surface running peripherally of the handle.

4 Claims, 4 Drawing Sheets

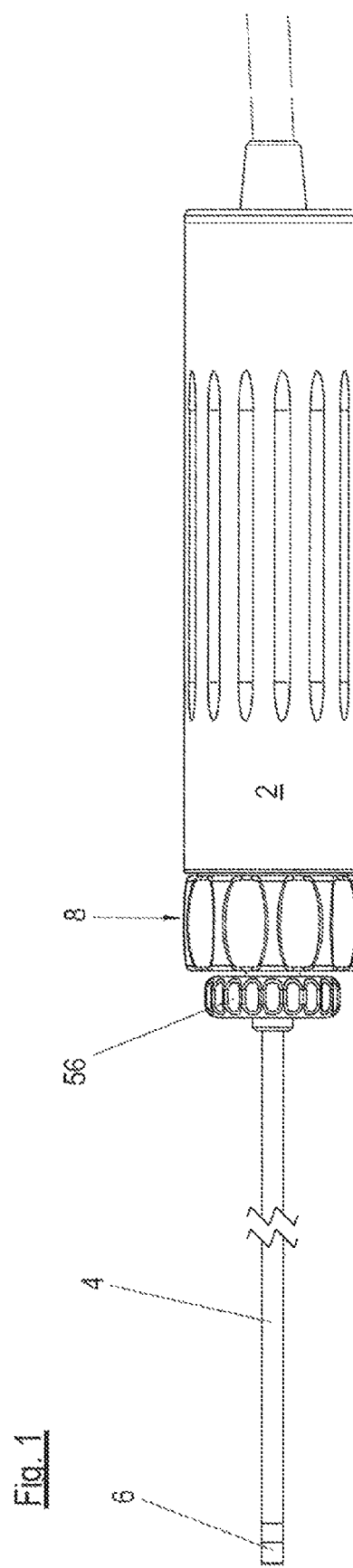

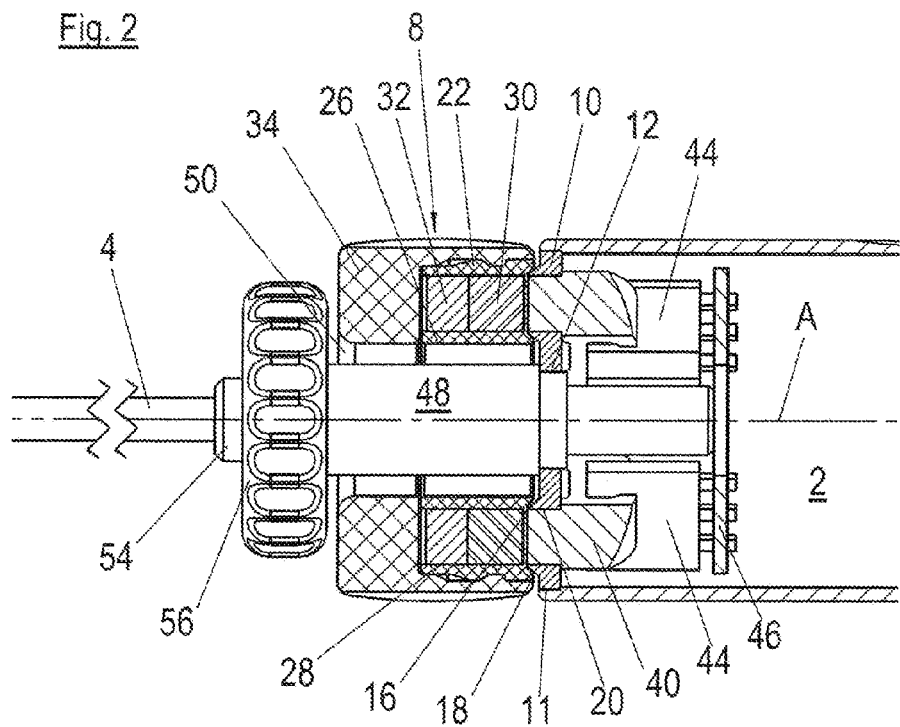
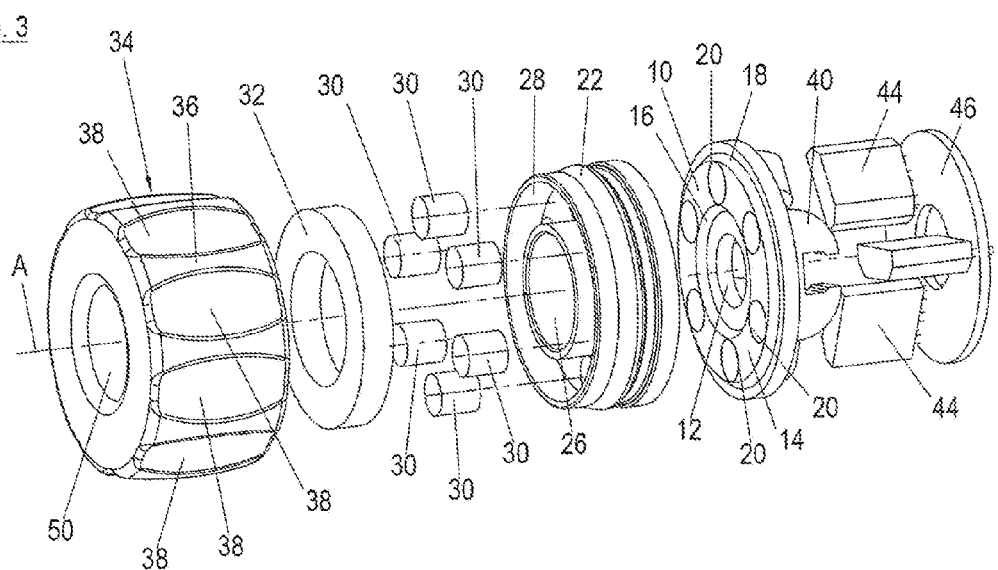

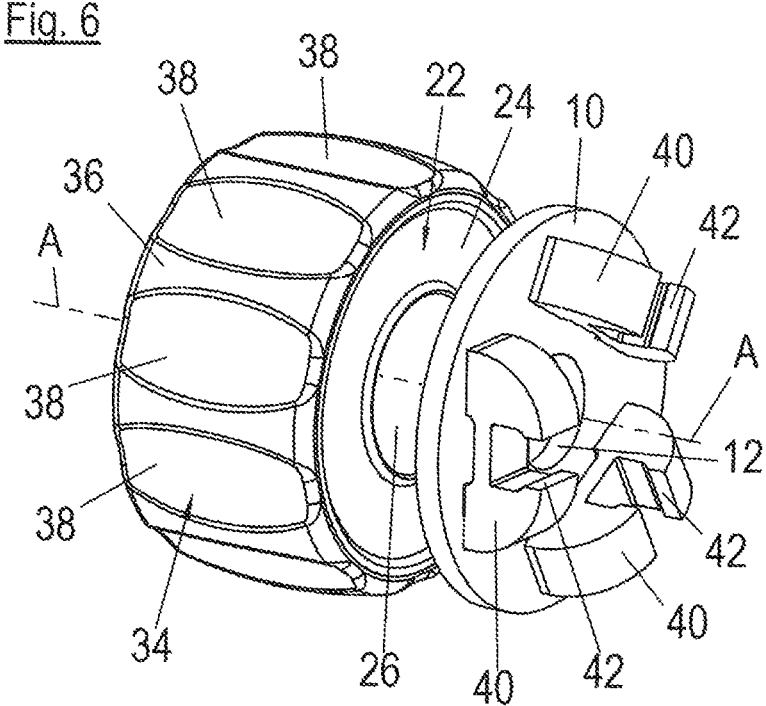

MEDICAL INSTRUMENT

BACKGROUND OF THE INVENTION

A multitude of instruments are used in the field of medicine, which include a proximal handle with one or more electrical switches arranged on the handle. Amongst these are video endoscopes, for example, with which several electric switches are arranged on a housing which connects proximally to a shank and which also serves as a handle. For example, picture representation parameters can be changed with these switches. With the application of video-endoscopes, it is often necessary to rotate the endoscope about the longitudinal axis of its shank. The position of the switches arranged on the housing of the endoscope relative to the endoscope user compellingly changes by way of such a rotation of the video endoscope. Under certain circumstances, this can result in the user of the video endoscope having to change his grip position on the housing, or having to use both hands, in order to actuate the switches. This renders the operation of video endoscopes quite awkward.

Against the above background, it is an objective of a preferred embodiment of the present invention to provide a medical instrument with which electrical switches arranged on a proximal handle can be easily actuated independently of a rotational position of the instrument or of the handle.

BRIEF SUMMARY OF THE INVENTION

The above objective is achieved by a medical instrument with a handle, on which at least one electric switch is arranged, wherein the switch includes an annular mechanical actuation unit whose outer side forms a grip surface running peripherally of the handle. Advantageous further developments of this instrument are to be deduced from the subsequent description as well as the drawings. Hereby, according to a preferred embodiment of the present invention, the features specified in the dependent claims in each case per se, but also in a technically meaningful combination can further form the solution according to the present invention and according to the independent claim(s).

The medical instrument according to a preferred embodiment of the present invention has a handle, on which at least one electrical switch is arranged. According to the basic idea of a preferred embodiment of the present invention, this switch includes an annular mechanical actuation unit, whose outer side forms a grip surface running peripherally of the handle. This grip surface is always accessible independently of the rotational position of the handle, wherein the mechanical actuation unit of the switch via a manual exertion of force effected at any peripheral position of the grip surface, can activate a switching operation. Inasmuch as this is concerned, the medical instrument according to the invention can have a significantly improved user-friendliness or ergonomy compared with known instruments of the type being discussed here and which have been known until now.

The at least one electrical switch of the instrument according to a preferred embodiment of the present invention can be integrated into the handle of the instrument, thus can be arranged within the handle or can be arranged at least partly on an end of a handle, preferably on its distal end. An arrangement of the switch on the outer side of the handle has the advantage that the disassembly of the switch, for example for cleaning the medical instrument or for maintenance purposes, is considerably simpler, since with a suitable design, it is not necessary to open the handle for removing the switch.

The at least one electric switch arranged on the handle can advantageously be a push switch. Accordingly, a switching procedure can be activated by it by way of exerting a push force onto the grip surface. Hereby, a design is preferred, with which the switch reacts independently of the acting direction of the push force exerted on the grip surface. In order to be able to actuate a switching procedure by way of such push forces, the annular mechanical actuation unit of the switch, for example, as a whole, can be arranged in a movable manner in the radial direction and by way of its radial movement can effect a switching procedure in a direct manner or indirectly via a mechanical coupling element or via a suitable sensor in the electrical part of the switch. For this, the actuation unit is arranged usefully with a certain radial play to the electrical part of the switch which is arranged within the actuation unit, or with radial play to mechanical coupling elements which, as the case may be, on the inner side are adjacent the actuation element, or to sensors for the control of the electric part of the switch. In one preferred embodiment of the present invention, the mechanical actuating unit is hereby elastically mounted in the radial direction on an elastomer mounting or on spring elements, in order after an actuation of the switch, to be able to return again into a normal position, in which it again has a radial play to the electric part or to the mechanical coupling elements or sensors. Apart from this, the actuation unit can also be arranged an axially displaceable manner and be moved by way of a suitable exertion of pressure onto the actuation unit, from a first switch position into a second switch position.

Instead of being designed as a push switch, the at least one electrical switch of the medical instrument according to a preferred embodiment of the present invention can advantageously also be designed as a rotary switch. In this case, the annular mechanical actuation unit is rotatably arranged on the handle. Preferably, the rotary switch is rotatable in two opposite directions, wherein in each case at least one switching function can be assigned to each of the two rotation directions. Further advantageously, the rotary switch can comprise a locking device which permits the actuation unit to rotate into several defined locking positions, to which in each case different switch functions can be assigned as the case may be. Moreover, a stepwise or continuous changing of electrical variables is made possible with a switch designed as a rotary switch. Also with the electric switch designed as a rotary switch, the mechanical actuation unit by way of its movement, in the present case by way of its rotation movement, can effect a switching procedure in a direct manner or indirectly via a suitable sensor in the electric part of the switch.

A combined push and rotary switch is advantageously provided as a switch. For example, with the annular mechanical actuation unit, one can carry out a first switching function by way of radial pressure on any location of the grip surface and at least one further switching function by way of rotating the actuation unit, where here too a design is preferably envisaged, with which different switching functions can be carried out in dependence on the rotation direction of the actuation unit. Usefully, with a design of the switch as a push and rotary switch, the mechanical actuation unit is designed displaceable in the radial direction as well as rotatable about a rotation axis.

As has already been noted, the at least one electrical switch can be designed in a manner such that the mechanical actuation unit acts directly on the electric part of the switch and activates a switching operation there. Thus, with a switch designed as a push switch, for example, the actuation unit with its radial movement can act in a direct mechanical manner on a switch contact in the electrical part of the switch and close or open this switch contact. With a switch designed as a rotary switch, the actuation unit can for example form a part of a sliding contact and in this manner carry out a switching operation. Hereby, a radial inner side of the annular actuation unit forms a slider, or a sliding ring connected to the actuation unit is arranged on the radial inner side of the actuation unit.

Preferably however, one envisages the mechanical actuation unit of the electrical switch acting indirectly on the electrical part of the switch. In this case, at least one sensor is arranged between the actuation unit and the electric part of the switch, and this sensor for example detects a movement of the actuation unit or a pressure exerted by the actuation unit onto the sensor and hereupon produces a switch signal or control signal in the electrical part of the switch and thus initiates a switching operation. Preferably, several sensors are arranged between the actuation unit and the electrical part. These sensors can be designed in an equal manner or it can be the case of different sensors. This arrangement has the advantage that the actuation unit and the electric components of the switch can be separated from one another. Thus the electric components can be completely encapsulated, so that an unproblematic cleaning of the instrument is possible. The moving parts, specifically the actuation unit, transmit their movement onto the electrical components only in an indirect manner via the sensors. Thereby, the sensors are preferably designed such that they can detect the movement through a closed wall. The actuation unit can preferably be designed in a removable manner for cleaning purposes.

Thus advantageously, at least one electric sensor can be arranged between the mechanical actuation unit and the electric components of the switch. With regard to this electronic sensor, it can be case of such a sensor which detects a resistance change caused by a movement of the actuation unit relative to the sensor or by a pressure exerted from the actuation unit onto the sensor, and hereupon transmits a control signal to the electric components of the switch. Moreover, the electrical sensor can be such a sensor which detects a change of capacitance or a change of inductance, which is caused in it by way of the movement of the actuation unit, and converts this change into a control signal for the electric components of the switch.

In an alternative advantageous design, at least one optoelectronic sensor can be arranged between the mechanical actuation unit and the electric components of the switch. Thus, for example, with an electrical switch designed as a rotary switch, at least one photodiode can be arranged directly on the inside of the actuation unit, for example, lying directly opposite the inner wall of the actuation unit, and at least one ring section of the actuation unit is designed in a transparent manner, so that when the transparent section of the actuation unit is moved over the photodiode on rotation of the actuation unit, an electrical signal is produced in the photodiode and as a control signal for a switching operation is led to the electrical components of the switch.

According to a further advantageous design, at least one piezoelectric sensor can be arranged between the mechanical actuation unit and the electrical components of the switch. This design is particularly favorable with an electrical switch designed as a push switch. In this case for example a multitude of piezoelements can be arranged forming a ring, on the inside of the actuation unit and the inner wall of the actuation unit. A pressure acting on the piezoelement which is produced on it with a radial movement of the actuation unit produces a voltage in the piezoelements which can be used as a control signal for the electric components of the switch.

Particularly advantageously, at least one magnetic sensor can be arranged between the mechanical actuation unit and the electrical components of the switch. This sensor is usefully arranged on a stationary, for example, non-moving part of the switch and preferably in the handle. The sensor is signal-connected to the electrical components which are advantageously likewise arranged on the handle, for controlling the switch. The sensor detects changes of the magnetic flux density of a magnetic circuit which is formed by components which are arranged in the actuation unit in a movable manner and stationary components preferably arranged in the handle. In the simplest case, the magnetic circuit can be formed by a permanent magnet arranged in the actuation device and a stationarily arranged magnet sensor. Preferably, the permanent magnet and the magnet sensor or the sensor with ferromagnetic yoke elements is arranged such that at least one closed magnetic circuit is formed. This magnetic circuit is only closed at a certain rotation position of the actuation element. With a rotation movement of the actuation unit out of this rotation position, the permanent magnet or the components which are arranged in the actuation unit and form part of the magnetic circuit are moved relative to a stationary yoke element, by which means the magnetic circuit or the magnetic flux density detected by the sensor changes or is reduced. Inasmuch as this is concerned, for example, two switch positions can be defined with the switch, specifically one, in which a closed magnetic circuit with a maximal magnetic flux density is present, and a further switch position, in which the magnetic circuit is broken up and the magnetic flux density is accordingly reduced. A particular advantage of the use of a magnetic sensor it to be seen in the fact that all electric and electronic components of the switch can be arranged in a hermetically closed handle and only the mechanical components of the switch, for example, the actuation unit are arranged outside the handle. Moreover, the actuation unit, in the best case, is held on the handle alone by way of the magnetic force acting in the magnetic circuit. This is of particular significance with regard to the cleaning of the medical instrument. For this, the actuation unit can be removed from the handle in a simple manner. This permits a complete cleaning of all surfaces of the actuation unit and handle.

The greatest magnetic holding force between the magnetic components arranged in the actuation unit and the stationarily arranged magnetic components exists in the rotation position of the actuation unit, in which the magnetic components which are arranged in the actuation unit and the magnetic components arranged stationarily on the grip form a closed magnetic circuit, and this greatest magnetic holding force holds the magnetic components in this position and thus quasi effects a locking. A force which is larger than the magnetic holding force must be exerted onto the actuation unit, in order to move the actuation element out of this locking position. Thus a locking is simultaneously achieved via the magnetic coupling.

With the design of the switch, with which at least one magnetic sensor is arranged between the mechanical actuation element and the electric components of the switch, the actuation unit comprises at least one, preferably however two or more rod magnets which are magnetically connected via a preferably ferromagnetically designed first yoke element and which are movable relative to a second yoke element arranged in the handle in a stationary manner and likewise being preferably ferromagnetic. Hereby, the rod magnets are arranged in the movable actuation unit in a manner such that in at least one rotational position of the actuation element, the end-faces of the rod magnets are aligned with the end-faces of the yoke elements arranged stationarily in the handle, said latter end-faces being directed to the actuation unit. The ferromagnetic yoke element in the actuation unit is designed in a manner such that together with the magnets in the actuation unit and the yoke elements arranged in the handle, it forms at least one closed magnetic circuit with at least one rotational position.

With regard to design, it is advantageous if a multitude of rod magnets is distributed over the periphery of the switch. Usefully, in each case adjacent rod magnets in the actuation unit are arranged with an alternating alignment of the polarity and are connected to a ferromagnetic yoke element which is adjacent the end-faces of the magnets. Stationary, second yoke elements which with a suitable rotational position of the actuation unit form closed magnetic circuits with the magnets and the yoke element of the actuation unit are arranged in the switch in a manner corresponding to the number of magnet pairs in the actuation unit. A difference between the magnetic flux densities in the individual magnetic circuits always exists if not all magnets in the actuation unit are arranged exactly aligned to the end-faces of the yoke elements in the handle, but are arranged more or less offset. These differences, as the case may be, can be detected on each yoke element in the handle and thus permit the realization of several switch positions of the switch, or also permit recognition of the rotation direction.

Preferably, a sensor for detecting a magnetic field is arranged on the at least one, second stationary yoke element, for detecting magnetic field changes or for detecting changes of magnetic flux density, with a movement of the actuation unit. Basically, all sensors capable of detecting the magnetic flux density are suitable as sensors, but a Hall sensor is preferably applied.

Advantageously, with regard to the medical instrument according to a preferred embodiment of the present invention, it can be the case of an endoscope and preferably of a video endoscope. Since endoscopes often need to be rotated when examining a region which is to be examined and which lies in the inside of the body, with these instruments, it has be found to be particularly advantageous if the switches to be provided on the handle of these instruments are designed in the manner according to the invention, which makes the work easier for the operator of the endoscope, in comparison to endoscopes known until now.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a schematically simplified lateral view of an endoscope in accordance with a preferred embodiment of the present invention;

FIG. 2 is an enlarged, partly sectioned view a part region of a handle of the endoscope of FIG. 1;

FIG. 3 is a perspective exploded representation of a switch of the endoscope of FIG. 1;

FIG. 6 in a further perspective exploded representation of the switch of FIG. 3.

DETAILED DESCRIPTION OF THE INVENTION

Certain terminology is used in the following description for convenience only and is not limiting. The words "inwardly" and "outwardly" refer to directions toward and away from, respectively, the geometric center of the device, and designated parts thereof, in accordance with the present invention. Unless specifically set forth herein, the terms "a," "an" and "the" are not limited to one element, but instead should be read as meaning "at least one." The terminology includes the words noted above, derivatives thereof and words of similar import.

Figure 4:
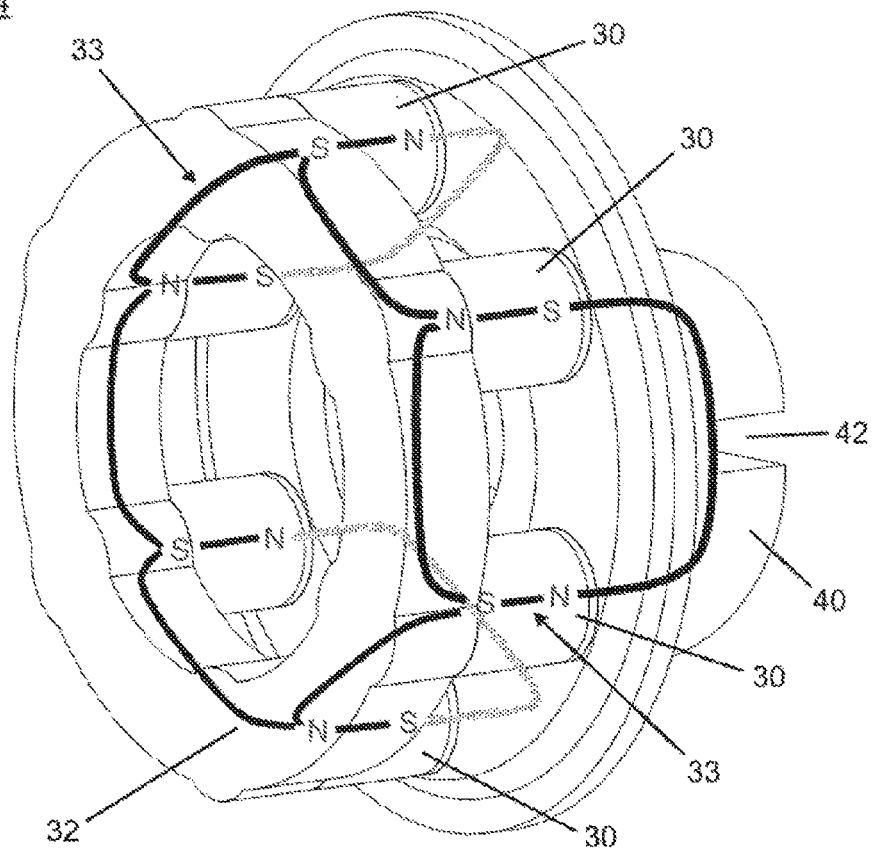
FIG. 4 is a basic representation of a magnetic flux in the switch of FIG. 3.
Figure 5:
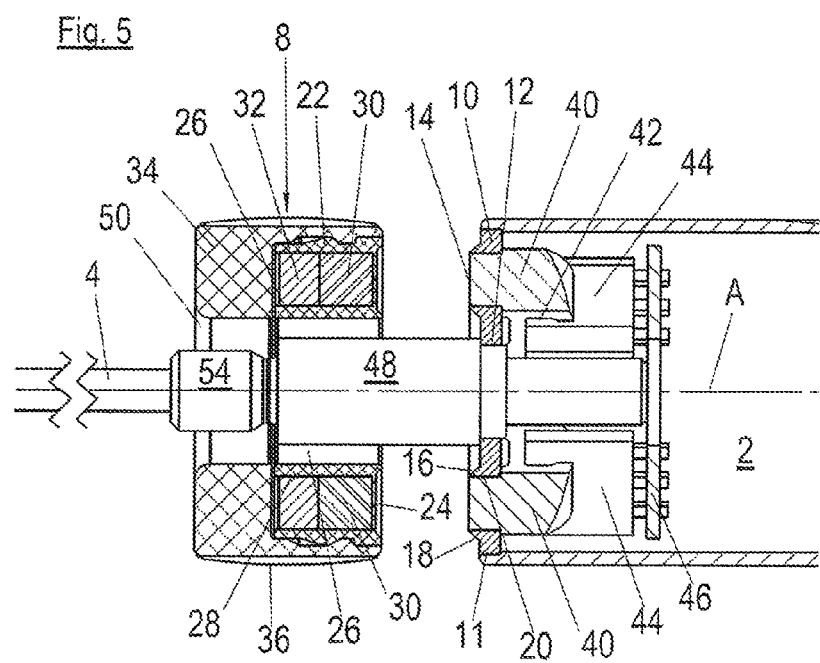
FIG. 5 is an enlarged lateral view of the switch of FIG. 3.

Referring to the drawings in detail, wherein like numerals indicate like elements throughout the several views, FIG. 1 shows an endoscope that is preferably in the form of a video endoscope. The video endoscope preferably includes a housing which forms a handle 2 of the video endoscope. A shank 4 connects to the handle 2 at the distal side. A picture acquisition unit and an illumination means of the videoscope are arranged on a distal end 6 of the shank 4, for example, in the usual manner. The handle 2 is designed in a cylindrical manner. At its distal end-side, a mechanical actuation unit 8 of an electrical switch is arranged on the handle 2. The exact construction of this switch is hereinafter explained by way of FIGS. 2-6.

The distal end of the handle 2 which is designed in a hollow-cylindrical manner is closed by a disk-like end-part 10. Hereby, the end-part 10 lies on a shoulder 11 which is formed at the distal end of the inner wall of the handle 2, wherein the end-part 10 is connected to the inner wall of the handle 2 in a hermetically sealed manner.

Centrally, a circular opening 12 is formed on the end-part 10 which is formed from a non-magnetic material. This opening 12 at the side of the end-part 10 which is away from the handle 2 is surrounded by an annular prominence 14 arranged concentrically to it and extending in the distal direction. An inner edge 16 of the prominence 14 is designed beveled obliquely outwardly in the distal direction with respect to the middle axis A of the endoscope. Moreover, an outer edge 18 of the prominence 14 is designed beveled obliquely inwardly in the distal direction with respect to the middle axis A. In the region of the prominence 14, six circular openings 20 are formed on the end-part 10 in a manner distributed uniformly over its periphery. The ends of three ferromagnetic, arch-shaped yoke elements 40 are arranged in these opening 20 and are connected to the end-part 10 in a hermetically sealed manner. The end-faces of the yoke elements 40 thus together with the end-face of the prominence 14 form a plane surface.

A sliding ring 22 (similar to a slip ring) connects to the end-part 10 at the distal side. An annular recess 24 is formed on this sliding ring 22 on the proximal end-face of this sliding ring, and the position, width and outer edges of this recess correspond to the position, width and design of the edges of the prominence 14 on the end-part 10. The sliding ring 22 is rotatably mounted on the end-part 10, wherein the prominence 14 formed on the end-part 10 engages into the recess 24 formed on the sliding ring 22.

Departing from the distal end-side of the sliding ring 22, an annular groove 28 extends in the proximal direction peripherally of a central opening 26. The annular groove 28 serves for receiving six cylindrical rod magnets 30 which are uniformly distributed in the annular groove 28 over its periphery. The rod magnets 30 are magnetized in the longitudinal direction, for example, their poles are each located at the end-sides which are away from one another. The successive rod magnets 30 have an alternatingly arranged poling. For example, if a first rod magnet 30 is arranged such that the north pole is located on the distal side, the adjacent rod magnet is arranged such that the south pole is located at the distal side. Then, with the following rod magnet, the north pole is again located on the distal side, etc.

The annular groove 28 also serves for receiving a first yoke element 32, whose inner diameter and outer diameter correspond to the inner diameter and outer diameter of the annular groove 28. The yoke element 32 is formed from a ferromagnetic material and lies on the rod magnet 30 on the face side. With a suitable rotational position of the sliding ring 22, closed magnetic circuits are formed by way of the yoke element 32, the rod elements 30 as well as the yoke elements 40, in accordance with the field lines represented in FIG. 4.

The sliding ring 22 is surrounded by a grip ring 34 on the outer side. The radial outer side of the grip ring 34 forms a grip surface 36. Recesses 38 are formed on the grip surface 36 in a manner running distributed over its periphery distributed at regular distances parallel to the middle axis A, for an improved handling of the grip part 34.

Together, the sliding ring 22 with the rod magnets 30 arranged therein and the yoke element 34 as well as the grip ring 34 forms the mechanical actuation unit 8 of the electrical switch. For this, the sliding ring 22 with the rod magnets 30 arranged therein and with the yoke element are pressed with the grip ring 34 and sealingly bonded.

The openings 20 formed on the end-part 10 are envisaged for receiving the ends of yoke elements 40 designed in an arch-shaped manner. Hereby, the ends of three yoke elements 40, departing from the proximal end-side of the end-part 10, engage in each case into two adjacent openings 20. The yoke elements 40 are formed from a ferromagnetic material.

The yoke elements 40 on their outer apex region in each case comprise a groove 42. These grooves 42 in each case serve for receiving a Hall sensor 44. The Hall sensors 44 are arranged on a carrier circuit board 46 which, in a manner not shown in the drawings, can carry further electrical components of the switch which are arranged in the handle 2.

A receiver part 48 for receiving the hollow shank 4 of the endoscope is arranged in the opening 12 of the end-part 10 and is hermetically sealing connected to the end-part 10 and the hollow shank 4. The receiver part 48 engages through the opening 26 formed on the sliding ring 22 and through an opening 50 formed on the sliding ring 34. The receiver part 48, at the distal end, tapers into a shoulder 54 projecting at the distal side out of the grip part 34. An outer thread is formed on the shoulder 54. A knurled nut 56 is screwed on this outer thread. The knurled nut 56 serves for securing the mechanical actuation unit 8 of the switch on the handle 2.

The manner of functioning of the electric switch is as follows:

The annular mechanical actuation unit 8 is rotatable about the middle axis A of the endoscope, in a first direction and in a second direction which is opposite to this, by way of the rotatable mounting of the sliding ring 22 on the end-part 10.

If on assembly of the actuation unit 8, this is placed onto the endoscope, the magnetic field of the magnets 30 in the actuation unit 8 approaches the ferromagnetic yoke elements 40 in the end-part 10. The resulting forces between the magnet 30 and the yoke elements 40 ensure that the actuation unit 8 is pulled onto the end-part 10, until the surface of the recess 24 of the sliding ring 22 lies on the surface of the prominence 14 of the end-part 10. Additionally, the mentioned forces ensure a positioning of the actuation unit 8 with regard to its rotation position, in a manner such that the magnets 30 are aligned as best as possible with the yoke elements 40 in the handle. In this position, the field lines 33 run through the ferromagnetic material of the yoke elements 32 and 40 in the best possible manner and the holding force of the magnets is maximal. This rotational position is detected by the Hall sensors 44 and the electronics located on the carrier circuit board 46, by way of the then largest magnetic flux. In the described first basic position, the actuation unit 8 is held on account of the acting magnetic force, as long as no forces act externally on the actuation unit 8.

If the actuation unit 8 rotates out of the described basic position while overcoming the holding moment, the existing magnetic circuits through the ferromagnetic yoke elements 40 are increasingly broken up until the magnets 30 arranged in the sliding ring 22 approach the end-faces of the yoke elements 40 which are nextly adjacent in the rotation direction. The magnetic circuits build up again on approaching these end-faces of the yoke elements 40 which are next in the rotation direction, until the end-faces of the yoke elements 40 again are aligned as best as possible with the end-faces of the magnets 30. The magnetic force is now again at its maximum and the actuation unit 8 is held in its second basic position. Since adjacent magnets have a poling which is arranged in an alternating manner, as has already been described, the direction of the magnetic field in the yoke elements 40 is in each case reversed by way of the rotation of the actuation unit 8 from the first into the described second basic position. The rotation of the actuation unit 8 is detected by the Hall sensors 44 and by the electronics located on the carrier circuit board 46, on account of the reversal of the magnetic field, and is transferred to the electric components of the switch for a first switching procedure.

In order to permit rotational direction recognition with the switching procedure, the magnets are not arranged with a regularly alternating alignment of the poling, but in a sequential sequence with regard to the poling. Further possibilities for rotation direction recognition can be provided by way of the succession of magnets having a missing location or the strength of the resulting magnetic fields being able to vary. Thus different switching functions can be assigned to the different rotation directions.

The actuation unit 8 is also deflected out of one of the mentioned basic positions with a pressure application on the grip surface 36 in the radial direction of the actuation element 8, wherein the magnets 30 arranged in the actuation unit 8 are moved relative to the yoke elements arranged on the end-part 10. Hereby, the obliquely aligned edges of the prominence 14 on the end-part and of the recess 24 on the sliding ring 22 have the effect that the sliding ring 22 is not only moved in the radial direction, but also in the direction of the middle axis A, away from the end-part 10 and the yoke elements 40 arranged thereon. This, apart from the shifting of the magnets 30 to the end-faces of the yoke elements 40, additionally leads to an air gap between the actuation unit 8 and the end-part 10. This results in a reduction of the magnetic flux density in the magnetic circuits. After completion of the pressure application on the actuation unit, the actuation unit 8 on account of the acting magnetic forces centers itself again in the basic position and the flux density again reaches the initial value of the basic position. Since the actuation element does not rotate with a radial pressure application, no reversal of the magnetic poling takes place in the yoke elements 40. The mentioned changes of the magnetic field are detected by the Hall sensors, whereupon a control signal for a second switching operation is transmitted from the electronics located on the carrier circuit board 46 to the electrical components of the switch.

The knurled nut 56 is screwed off from the shoulder 54 for cleaning the represented endoscope. The actuation unit 8 although then still being held on the end-part 10 of the handle 2 by way of the acting magnetic forces, however can be pulled away from this when overcoming the magnetic forces. Moreover, the actuation unit 8 can be cleaned separately from the handle 2, wherein all surfaces of the actuation unit 8 and of the handle 2 are accessible. After the cleaning, the actuation unit 8 is again placed onto the end-part 10 of the handle 2, wherein this end-part automatically aligns itself on account of the tendency of the magnets 30 in the actuation element 8 to form closed magnetic circuits with the yoke elements 40 arranged on the proximal side of the end-part 10. Finally, the knurled nut 56 is screwed onto the shoulder 54 again for securing the actuation element 8 on the end-side 10 of the handle 2.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. An endoscope comprising:
   a handle (2); and
   at least one electric switch arranged on the handle, the switch comprising an annular mechanical actuation unit (8), an outer side of the annular mechanical actuation unit forming a grip surface (36) running peripherally of the handle (2), the switch further comprising two rod magnets (30) magnetically connected via a first yoke element (32) and movable relative to a stationarily arranged second yoke element (40), the first yoke element (32) being formed of a ferromagnetic material, the switch being a combined push and rotary switch wherein the mechanical actuation unit (8) is displaceable in a radial direction as well as rotatable about a rotation axis,
   wherein a magnetic sensor is arranged between the mechanical actuation unit (8) and electric components of the switch.

2. The endoscope according to claim 1, wherein a multitude of rod magnets (30) are distributed over a periphery of the switch.

3. The endoscope according to claim 1, wherein adjacent rod magnets (30) have an alternatingly arranged poling.

4. The endoscope according to claim 1, wherein a sensor for detecting a magnetic field is arranged on the second yoke element (40).

* * * * *